United States Patent [19]

Li et al.

[11] Patent Number: 5,643,498
[45] Date of Patent: Jul. 1, 1997

[54] QUATERNARY CATIONIC SURFACTANTS HAVING MULTIPLE HYDROPHOBIC AND HYDROPHILIC GROUPS

[75] Inventors: Ji Li, East Windsor; Manilal Dahanayake, Princeton Junction; Robert Lee Reierson, Cranbury; David James Tracy, Plainsboro, all of N.J.

[73] Assignee: Rhone-Poulenc Inc., Cranbury, N.J.

[21] Appl. No.: 292,896

[22] Filed: Aug. 19, 1994

[51] Int. Cl.$^6$ .................. C07D 403/12; C07D 403/10; B01F 17/18; B01F 17/32
[52] U.S. Cl. ........................................ 252/357; 548/313.7
[58] Field of Search ........................ 548/313.7; 252/357

[56] References Cited

U.S. PATENT DOCUMENTS

| | | | |
|---|---|---|---|
| 2,524,218 | 10/1950 | Bersworth | 252/117 |
| 2,532,391 | 12/1950 | Bersworth | 260/404.5 |
| 3,033,704 | 5/1962 | Sherrill et al. | 117/47 |
| 3,095,373 | 6/1963 | Blomfield | 252/8.8 |
| 3,855,235 | 12/1974 | McConnell | 260/309.6 |
| 3,887,476 | 6/1975 | McConnell | 252/8.75 |
| 3,898,244 | 8/1975 | McConnell | 260/309.6 |
| 4,720,383 | 1/1988 | Drach et al. | 424/70 |
| 4,758,671 | 7/1988 | Dvorsk et al. | 548/341 |
| 4,873,003 | 10/1989 | O'Lenick, Jr. et al. | 252/8.75 |
| 5,298,242 | 3/1994 | Vanlerberghe et al. | 424/78.36 |

FOREIGN PATENT DOCUMENTS 1407134  9/1975  United Kingdom .

OTHER PUBLICATIONS

Martell et al. Journal American Chemical Society, Dec. (1950), 72, pp. 5357–5361.
PPG Mazer Chemicals Technical Bulletin.

*Primary Examiner*—Johann Richter
*Assistant Examiner*—Laura L. Stockton
*Attorney, Agent, or Firm*—Paul J. Juettner; Craig M. Bell

[57] ABSTRACT

According to the invention, an improved class of quaternary cationic surfactants having two imidazolinium groups have been provided comprising compounds of the formula:

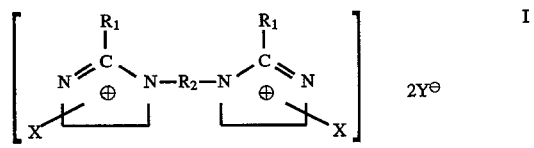

The surfactants of the subject invention have two hydrophobic moieties and two hydrophilic groups per molecule and are useful as hair and fabric conditioners as well as biocidal agents.

20 Claims, No Drawings

QUATERNARY CATIONIC SURFACTANTS HAVING MULTIPLE HYDROPHOBIC AND HYDROPHILIC GROUPS

This invention relates to quaternary imidazolinium cationic surfactants having two quaternary cationic groups per molecule.

BACKGROUND OF THE INVENTION

This invention relates to the production of quaternary imidazolinium agents which can be used for fabric conditioners, hair conditioners and biocides essentially free of primary and secondary amine salts.

In conventional home laundering, fabric conditioning agents are often added in the rinse cycle. The most favored type of agent has been the quaternary ammonium compounds. Additionally, imidazolinium salts have been used by themselves in the treatment of fabrics.

However, imidazolinium salts if made with polyamines can result in a final product that reacts with the aldehydes of perfume to decrease the effectiveness of that additive.

Generally, the manufacture of imidazolinium compounds involves the reaction of polyamines with an acyl compound or ester to form an imidazoline which is subsequently quaternized. In forming the original imidazoline, primary and secondary amines remain. During the subsequent quaternization step, these amines cause some of the imidazoline compound to form imidazoline amine rather than the salt. The imidazoline salt, when present in an aqueous medium having a near neutral or higher pH, is capable of undergoing ring opening to form free amines that can react with aldehydes. While the undesirable amines can be capped, it has now been found that an imidazoline quaternary compound can be made that does not require capping.

SUMMARY OF THE INVENTION

According to the invention, an improved class of quaternary cationic surfactants having improved surfactant properties have been provided which do not require capping and which do not contain any free primary or secondary amines. The compounds of the invention comprising compounds of the formula:

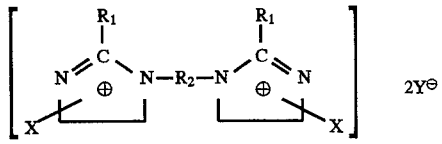   I wherein $R_1$ can independently be alkyl, hydroxy substituted or perfluorinated alkyl of from about 5 to about 22 carbon atoms; $R_2$ can be alkylene or alkylaryl of 1 to about 10 carbon atoms and the hydroxy substituted derivatives thereof or $R_3$—D—$R_3$ wherein $R_3$ can independently be alkylene of from 1 to about 6 carbon atoms and the hydroxy substituted derivatives thereof as well as aryl illustrated by phenylene, diphenylene and sulfonyldiphenylene, and D represents —O—, —S—, —$SO_2$—, a carbonyl group, a polyether group [—O($R_5$—O)$_x$—] or aryl wherein $R_5$ independently represents about $C_2$ to about $C_4$ alkyl with x being a number between 1 and 20 and y and z are independantly numbers from 1 to about 4; X can independently be alkyl of 1 to 10 carbon atoms and the hydroxy substituted derivatives thereof and alkylaryl; and Y independently represents an anion illustrated by halogen (Cl, Br, and I), alkylsulfate such as methyl or ethylsulfate, alkylphosphate such as methylphosphate and the like.

Preferably, the compounds of the present invention comprise those of Formula I in which $R_2$ is lower alkyl of from about 2 to about 4 carbon atoms and the hydroxy substituted derivatives thereof, X is lower alkyl of from 1 to 4 carbon atoms; and Y is halogen or methylsulfate.

In addition to new compounds, the invention also provides novel methods of preparing the same as well as new synergistic compositions when blended with other surfactants.

DETAILED DESCRIPTION OF THE INVENTION

While the compounds of the invention can be prepared by a variety of synthetic routes, it has been found that they can be produced particularly effectively by quaternizing a bisimidazoline prepared by a novel process disclosed and claimed in copending application "Amphoteric Surfactants having Multiple Hydrophobic and Hydrophilic Groups", Ser. No. 08/292,993 filed Aug. 19, 1994 (Attorney's Docket No. RD 94015) filed coextensively herewith wherein a polyamine reactant having at least four amino groups of which two are terminal primary amine groups is reacted with an acylating agent such as a carboxylic acid, ester, and the naturally occurring triglyceride esters thereof or acid chlorides thereof in an amount sufficient to provide at least about 1.8 fatty acid groups [$R_1C(O)$—] per polyamine to provide a bisimidazoline of the formula:

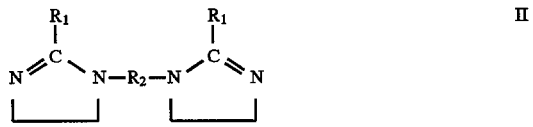   II

This reaction proceeds effectively at elevated temperatures (about 100° C.–250° C.) with continuous removal, such as by distillation, of the resulting condensate ($H_2O$) during the course of the reaction.

The progress of the reaction can be monitored by the amount of water recovered in the distillate. Two moles of water are generated for each imidazoline ring formed, one mole in the condensation reaction and one mole in the cyclodehydration reaction to form the imidazoline, hence double that for the bisimidazoline compounds of the invention. The process can be carried out with or without a catalyst, at atmospheric, reduced or super atmospheric pressure. The use of excess amine can result in undesirable by-products and is not recommended. Stoichiometric excess of fatty acid, ester, chloride or triglyceride can be used but is less desirable as it may require the need of a purification step to remove the excess.

In the compounds of Formulae I and II, $R_1$ can be derived from fatty acids, esters and triglycerides or the acid chlorides thereof from synthetic and natural sources which will generally contain mixtures of different carbon chain length saturated and unsaturated aliphatic radicals. The natural sources can be illustrated by coconut oil (preferred) or similar natural oil sources such as palm kernel oil, palm oil, soya oil, rapeseed oil, castor oil or animal fat sources such as herring oil and beef tallow. Generally, the fatty acids from natural sources in the form of the fatty acid or the triglyceride oil can be a mixture of alkyl radicals containing from about 5 to about 22 carbon atoms. In a more preferred material, the mixture of alkyl radicals can be derived from a saturated portion of coconut oil (from about 6 to about 18 carbon atoms) or similar natural vegetable oil. These ranges cover about 90% of the carbon chains in the compound. Since these fatty acids are derived from natural sources, they can contain small amounts of other carbon chains. Illustrative of the fatty acids in these oils are caprylic($C_8$), capric (10), lauric (12), myristic(14), palmitic(16), stearic (18), oleic (18, monounsaturated), linoleic (18, diunsaturated), linolenic (18, triunsaturated), ricinoleic (18, monounsaturated), arachidic (20), gadolic(20, monounsaturated), behenic (22) and erucic(22). These fatty acids can be used per se, as concentrated cuts or as fractionations of natural source acids. The fatty acids with even numbered carbon chain lengths are given as illustrative though the odd numbered fatty acids can also be used. In addition, single carboxylic acids, e.g., lauric acid, or other cuts, as suited for the particular application, may be used. Examples of acids derived from synthetic sources that can be used include 2-ethylhexanoic acid, pelargonic acid and the like.

The polyamine reactant has at least four amino groups of which two are terminal primary amine groups. The preferred polyamine is illustrated by triethylene tetramine (TETA). Other polyamines such as tetraethylenepentamine and others that would be obvious to one of skill in the art can also be used. The amine reactant can be defined by the structure:

III. 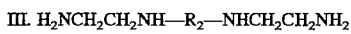

wherein $R_2$ is generally alkyl and aminoalkyl. The improved method of the invention will be illustrated with TETA but this is not intended to limit the invention to that starting material.

TETA is reacted with a sufficient amount of fatty acid to provide at least about 1.8 of fatty acid groups, preferably from about 1.9 to about 2.5 fatty acid groups, per molecule of polyamine to provide the bisimidazoline compound of the invention as in Formula I wherein $R_2$ is ethylene.

A second mode of synthesis of the bisimidazoline includes the steps of forming a single imidazoline such as from ethylenediamine and a fatty acid, ester, chloride or triglyceride. The fatty acids, esters, chloride or triglycerides thereof can be reacted with α,β- diamines in substantially equimolar quantities at temperatures ranging from about 150° to 250° C. with continuous removal of the resulting condensate ($H_2O$). The process can be carried out with excess amine, with or without a catalyst, at atmospheric, reduced or super atmospheric pressure.

The imidazoline can then be reacted with any difunctional compound that will join two of the imidazoline rings to form the bisimidazoline compound of the invention. These can be illustrated by any reactive dihalide, e.g., alpha, omega-dihalobutane, alpha, beta-dihaloethane, alpha, alpha'-dihaloparaxylene, diglycidyl ethers, diepoxides as well as epihalohydrins such as epichlorohydrin and the like.

In addition to alkyl and aminoalkyl groups contained in the examples of the poylamines given above, $R_2$ can thus be further illustrated by hydroxy-substituted alkyl such as—$CH_2CHOHCH_2$; an ether such as —$CH_2CH_2OCH_2CH_2$ or an alkylarylalkyl such as —$CH_2$—$C_6H_4$—$CH_2$—.

For reaction conditions generally, see JACS 67, 1581 (1945); U.S. Pat. Nos. 1,790,042; 1,845,403; JCS 1666 (1931), the disclosures of which are incorporated herein by reference. The reaction conditions must be such as to maintain the imidazoline ring structures.

The novel quaternary surfactants of the invention can be prepared of reacting the bisimidazoline with an alkylating agent in a known manner. The alkylating agent employed can be anyone of a number of known agents, such as alkyl halides illustrated by methylchloride, ethylbromide, and hexadecyl chloride; alkyl sulfates illustrated by dimethylsulfate, diethylsulfate as well as aryl chlorides such as benzyl chloride, chlorobenzyl chloride and dichlorobenzyl chloride, dimethylsulfate being preferred. In Formula I, X is an anion associated with the alkylating agent, representative anions including chloride, methylsulfate, ethylsulfate, and the like.

Equimolar quantities of the alkylating agent per imidazoline ring can be used but a slight excess of the alkylating agent is preferred to assure maximum quaternization. The excess of the alkylating agent is desirably sufficient to effect a pH in the reaction medium of from about 5 to about 7. The reaction temperature is desirably from about 40° to about 80° C. and from 1 to about 12 hours can be necessary to complete the reaction.

The surfactants of the invention can exhibit an extremely low critical micelle concentration (CMC) as compared with conventional surface-active agents because of the presence of two hydrophobic chains and two hydrophilic groups in their molecule. In addition, they are able to significantly reduce surface tension and are highly soluble in water. By virtue of these characteristics, they will find a wide variety of applications as emulsifiers, detergents, dispersant, and solubilizing agents for use in the fields of industrial, domestic, cosmetic, and medical goods.

While the surfactants of the invention can be used alone as the essential hydrotrope component, blends of the compounds of the invention with certain conventional well known anionic, nonionic, cationic and amphoteric surfactants can provide improved results beyond that expected which can be shown by the critical micelle concentration and the surface tension reducing ability of the blends.

Examples of the nonionic surfactants used herein include fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxyethylene lanolin alcohol, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oil or hardened castor oil derivatives, polyoxyethylene lanolin derivatives, polyoxyethylene fatty acid amides, polyoxyethylene alkyl amines, an alkylpyrrolidone, glucamides, alkylpolyglucosides, mono- and dialkanol amides, a polyoxyethylene alcohol mono- or diamides and alkylamine oxides. Examples of the anionic surfactants used herein include fatty acid soaps, ether carboxylic acids and salts thereof, alkane sulfonate salts, α-olefin sulfonate salts, sulfonate salts of higher fatty acid esters, higher alcohol sulfate ester salts, fatty alcohol ether sulfates salts, higher alcohol phosphate ester salts, fatty alcohol ether phosphate ester salts, condensates of higher fatty acids and amino acids, and collagen hydrolysate derivatives. Examples of the cationic surfactants used herein include an alkyltrimethylammonium salt, a dialkyl-dimethylammonium salt, an alkyldimethylbenzylammonium salt, an alkylpyridinium salt, an alkylisoquinolinium salt, benzethonium chloride, and an acylamino acid type cationic surfactant. Examples of the amphoteric surfactants used herein include amino acid, betaine, sultaine, phosphobetaine, an imidazoline type amphoteric surfactant, soybean phospholipid, and yolk lecithin.

In addition to the foregoing surfactants, any of commonly used auxiliary additives may be added to the surfactants of the invention or blends thereof with other surfactants as disclosed herein. Such auxiliary additives may be added to the surfactants of the invention on use. Such auxiliary additives may be suitably chosen for a desired composition and generally include inorganic salts such as Glauber salt and common salt, builders, humectants, solubilizing agents, UV absorbers, softeners, chelating agents, and viscosity modifiers.

The quaternary cationic surfactants of the present invention are useful in those areas where quaternary imidazoline compounds find use. These products are particularly useful for fabric and hair conditioners, and biocides.

Examples of the present invention are given below by way of illustration and not by way of limitation. All parts and percents are by weight.

EXAMPLES 1

Synthesis of Bisimidazoline of Compound II where $R_1$ is $C_{11}H_{23}$ and $R_2$ is ethylene To a 500 milliliter three-necked round bottom flask equipped with a stirrer, temperature controller, and a Barrett distilling receiver with a condenser on top were added 46.7 grams (0.25 mol) triethylene tetramine hydrate (average 2.1 to 2.2 moles water by Karl Fisher Analysis), 104 grams (0.52 mol) lauric acid and 100 milliliters toluene. The Barrett distilling receiver was filled up with toluene. The reaction mixture was gently heated with stirring to the boiling point of the toluene (120°–130° C.) and water collection was initiated.

The amount of water azeotroped with the toluene was determined. The first 20 milliliters which was collected in the first 3 hours of reaction indicated that the reaction was 70% complete. Water collection was continued.

The reaction temperature was slowly raised to 160°–180° C. during the 12 to 16th hour of reaction by releasing reactor-contained toluene from the Barrett distilling receiver. The progress of the reaction was also determined by gas chromatography. The disappearance of peaks corresponding to mon- and di- amides indicated completion of the condensation reaction.

After 16 hours of reaction, the reaction was stopped while 27.2 milliliters (28 milliliters calculated) of water had been collected. Gas chromatography showed that the 126 grams of product obtained contained greater than 96% of bisimidazoline (III).

The product was re-crystallized from $CHCl_3$ for structure characterization and identification. $^1H$ and $^{13}C$ NMR, IR, and Mass Spectra were recorded and the results agreed with the postulated structure.

EXAMPLE 2

Synthesis of Diguaternary of Compound I wherein $R_1$ is $C_{11}H_{23}$, $R_2$ is ethylene, X is $CH_3$, and Y is $CH_2SO_4$ To a 250 milliliter three-necked round bottom flask equipped with magnetic stirrer, temperature control and a condenser were added ethylene bis-laurimidazoline of Formula VII as prepared in Example 1 where $R_1$ is $C_{11}H_{23}$ (greater than 95% purity) and dimethyl sulfate in a 1:2 molar ratio and the solvent of choice as listed in the Table. The reaction mixture was heated to 50°–75° C. for 8 to 10 hours. An oily liquid was obtained which was very water soluble and exhibited good wetting and foaming properties. $^1H$ and $^{13}C$ NMR and IR characterizations confirm the structure as that postulated in Formula I. The parameters and results are shown in Table #2:

TABLE 2

| | | STARTING MATERIALS REACTION CONDITIONS | | | |
|---|---|---|---|---|---|
| RUN | PROD. EX. 1 (G) | $(CH_3O)_2SO_2$ (G) | SOLVENT (mL) | (°C./(h) | WEIGHT (G) | YIELD (%) |
| 1 | 4.74 | 2.52 | 20 (TOLUENE) | 75/6 | 7.3 | 100 |
| 2 | 4.74 | 2.52 | 30 ($CHCL_3$) | 60/6 | 7.3 | 100 |
| 3 | 14.22 | 7.56 | 70 ($CHCL_3$) | 6/8 | 22.2 | 100 |

For the compound of Example 2, the surface tension is 34 dynes/cm, the area of the molecule is 98 angstroms squared and the critical micelle concentration is $3.5 \times 10^{-5}M$ in 0.1M NaCl solution. This is 2–3 orders of magnitude lower than usually observed for quats. The pC-20 is also about 3 orders of magnitude better. This is the result of stearic hinderance inhibiting micellization (increased absorption). The diquaternary compound of the invention has excellent foaming properties.

The compounds of the invention can be used in fabric conditioners and these compositions are well known to one of skill in the art (See U.S. Pat. No. 4,127,489, the disclosure of which is incorporated herein by reference) and generally contain from about 1 to about 15% of the imidazolinium salt.

In addition to the quaternary imidazolinium salts of the invention, the fabric conditioner compositions using the compositions of the invention can contain other fabric conditioning agents such as further softening and antistatic agents. Conventional components of fabrics softeners can also be included such as clay materials, aldehyde preservatives, emulsifiers, thickeners, opacifiers, coloring agents, brighteners, fluoresces, pH adjustors, and perfumes. These fabric conditioning compositions can be used in the rinse cycle of a conventional laundry operation for achieving superior fabric softening and static control at levels of from about 2 ppm to about 500 ppm, preferably from about 10 ppm to about 100 ppm.

Although the subject invention has been described with respect to a preferred embodiment, it will be readily apparent to those having ordinary skill in the art to which the invention pertains that changes and modifications may be made thereto without departing from the spirit or scope of the subject invention as defined by the appended claims.

What is claimed is:

1. A surfactant selected from the group consisting of compounds of the formula:

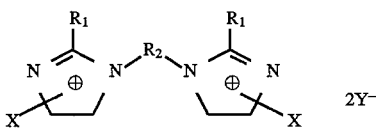

wherein $R_1$ independently represents alkyl, hydroxy substituted or perfluorinated alkyl of from about 5 to about 22 carbon atoms; $R_2$ represents hydroxy substituted alkylene or alkylaryl of 1 to about 10 carbon atoms and the hydroxy substituted derivatives thereof or $R_3$—D—$R_3$ wherein $R_3$ independently represents alkylene of from 1 to about 6 carbon atoms and the hydroxy substituted derivatives thereof as well as aryl, and D represents —O—, —S—, —$SO_2$—, a polyether group [—$O(R_4)_x$—] or aryl wherein $R_5$ independently represents about $C_2$ to about $C_4$ alkyl with x being a number from 1 to 20 and; X independently represents an alkyl of 1 to 10 carbon atoms and the hydroxy-substituted derivatives thereof and alkylaryl; and Y independently represents an anion.

2. The surfactant of claim 1, wherein $R_1$ is alkyl of from about 6 to about 18 carbon atoms.

3. The surfactant of claim 1, wherein $R_2$ represents the hydroxy substituted derivatives of lower alkylene of from 2 to about 6 carbon atoms.

4. The surfactant of claim 1, wherein the Y anion is halogen, alkylsulfate, and alkylphosphate.

5. The surfactant of claim 1, wherein the Y anion is chloride.

6. The surfactant of claim 1, wherein the Y anion is methyl or ethylsulfate.

7. A surfactant as recited in claim 1, wherein the Y anion is alkyl phosphate.

8. A surfactant as recited in claim 1, wherein $R_1$ is $C_5$–$C_{12}$ hydroxyalkyl or perfluorinated alkyl.

9. A surfactant as recited in claim 1, wherein X is $C_1$–$C_{10}$ hydroxyalkyl or alkylaryl.

10. A surfactant as recited in claim 1, wherein $R_2$ is $C_1$–$C_{10}$ hydroxyalkyl or alkylaryl.

11. A surfactant as recited in claim 1, wherein R2 is $R_3$—D—$R_3$ wherein D is —O—, —S— or a carbonyl group.

12. A surfactant as recited in claim 1, wherein $R_2$ is $R_3$—D—$R_3$ wherein $R_3$ is aryl.

13. A surface active composition comprising a surface actively effective mount of the compound of claim 1.

14. The surfactant of claim 1, further comprising a surfactant selected from the group consisting of an anionic, nonionic, cationic, and amphoteric surfactant.

15. The surfactant of claim 14, wherein said nonionic surfactant is selected from the group consisting of fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxyethylene lanolin alcohol, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oil or hardened castor oil derivatives, polyoxyethylene lanolin derivatives, polyoxyethylene fatty acid amides, polyoxyethylene alkyl amines, an alkylpyrrolidone, glucamides, alkylpolyglucosides, mono- and dialkanol amides, a polyoxyethylene alcohol mono- or diamides and alkylamine oxides.

16. The surfactant of claim 14 wherein said anionic surfactant is selected from the group consisting of fatty acid soaps, ether carboxylic acids and salts thereof, alkane sulfonate salts, α-olefin sulfonate salts, sulfonate salts of higher fatty acid esters, higher alcohol sulfate ester salts, fatty alcohol ether sulfates salts, higher alcohol phosphate ester salts, fatty alcohol ether phosphate ester salts, condensates of higher fatty acids and amino acids, and collagen hydrolysate derivatives.

17. The surfactant of claim 14, wherein said cationic surfactant is selected from the group consisting of an alkyltrimethylammonium salt, a dialkyl-dimethylammonium salt, an alkyldimethylbenzylammonium salt, an alkylpyridinium salt, an alkylisoquinolinium salt, benzethonium chloride, and an acylamino acid type cationic surfactant.

18. The surfactant of claim 14, wherein said amphoteric surfactant is selected from the group consisting of an amino acid, betaine, a sultane, phosphobetaine, an imidazoline type amphoteric surfactant, soybean phospholipid, and yolk lecithin.

19. The surfactant of claim 1, further comprising an auxiliary additive.

20. The surfactant of claim 19, wherein said auxiliary additive is selected from the group consisting of an inorganic salt a builder, a humectant, a solubilizing agent, a UV absorber, a softener, a chelating agent, and a viscosity modifier.

* * * * *